Figure 1:
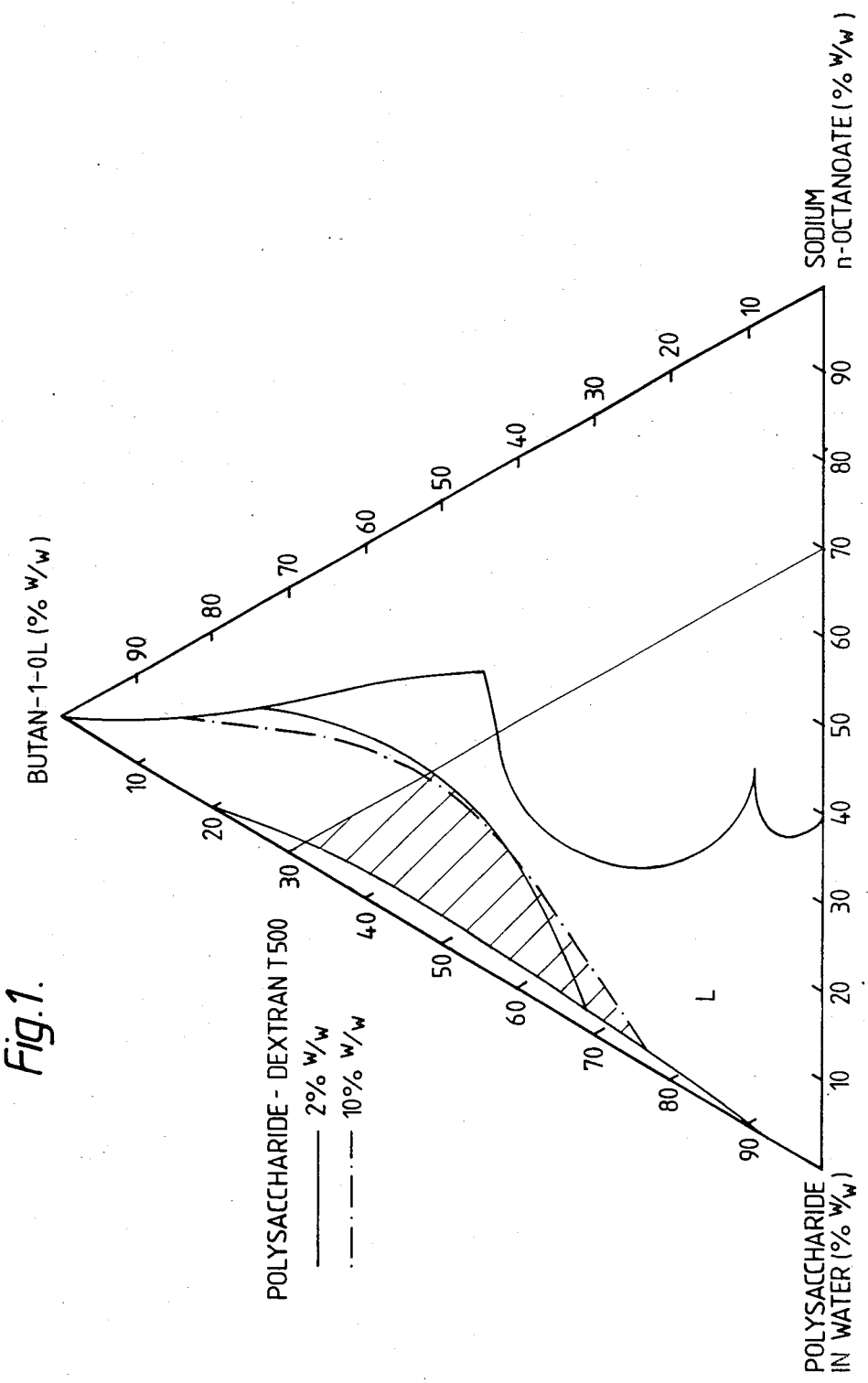

United States Patent [19]

Garvey et al.

[11] Patent Number: 4,810,787

[45] Date of Patent: Mar. 7, 1989

[54] PHASE SEPARATION OF POLYSACCHARIDES FROM AQUEOUS SOLUTIONS

[75] Inventors: Michael J. Garvey; Ian C. Griffiths, both of Merseyside, England

[73] Assignee: Internationale Octrooi Maatschappij "Octropa: BV, Rotterdam, Netherlands

[21] Appl. No.: 890,333

[22] Filed: Jul. 29, 1986

[30] Foreign Application Priority Data

Aug. 9, 1985 [GB] United Kingdom ............... 8520101

[51] Int. Cl.[4] .................. C08B 37/00; C07H 1/06; C07G 17/00
[52] U.S. Cl. ................................. 536/127; 536/1.1; 536/18.5; 536/55.3; 536/112; 536/114; 536/123; 536/124
[58] Field of Search .............. 536/18.5, 55.3, 112, 536/114, 123, 124, 127, 1.1

[56] References Cited

U.S. PATENT DOCUMENTS

| | | | |
|---|---|---|---|
| 3,900,462 | 8/1975 | Komatani et al. | 536/127 |
| 3,988,313 | 10/1976 | Bouniot | 536/127 |
| 4,129,722 | 12/1978 | Iovine et al. | 536/114 |
| 4,210,641 | 7/1980 | Brossard et al. | 536/123 |
| 4,307,084 | 12/1981 | Drabick et al. | 536/112 |
| 4,329,448 | 5/1982 | Cox et al. | 424/49 |
| 4,511,559 | 4/1985 | Szendrei et al. | 536/123 |
| 4,567,140 | 1/1986 | Voelskow et al. | 536/114 |
| 4,703,117 | 10/1987 | Fischer et al. | 536/114 |

FOREIGN PATENT DOCUMENTS

| | | | |
|---|---|---|---|
| 0612791 | 1/1961 | Canada | 536/112 |
| 0023397 | 4/1981 | European Pat. Off. | |
| 2835096 | 1/1979 | Fed. Rep. of Germany | |

OTHER PUBLICATIONS

Rosenholm et al., *Colloid & Polymer Sci.*, 225:1098–1109 (1977).

Primary Examiner—Ronald W. Griffin
Assistant Examiner—Nancy S. Carson
Attorney, Agent, or Firm—Cushman, Darby & Cushman

[57] ABSTRACT

This invention relates to a process for the separation of a polysaccharide from an aqueous system using a water-soluble fatty acid salt and optionally a precipitated liquid to separate out the polysaccharide.

7 Claims, 7 Drawing Sheets

PHASE SEPARATION OF POLYSACCHARIDES FROM AQUEOUS SOLUTIONS

This invention relates to the separation of polysaccharides from aqueous systems. More particularly, the invention relates to a phase separation technique which is useful in removing polysaccharides from dilute aqueous solutions.

BACKGROUND OF THE INVENTION

Many high molecular weight polysaccharides can be produced by biological reactions, see for example U.S. Pat. No 4,230,699, which relates to the preparation of a natural heteropolysaccharide and U.S. Pat. No 4,329,448, which relates to a novel heteropolysaccharide known as Biopolymer PS 87.

It will be apparent from these specifications and other art that such reactions produce the desired polysaccharide in a dilute concentration. Proposals have been made in the prior art to separate out the polysaccharide from the aqueous medium by, for example, the addition of a large quantity of a water-miscible alcohol which precipitates out the polysaccharide. Other proposals for separation require additional steps to the use of a water-miscible solvent such as those described in U.S. Pat. No 4,230,699, in which the precipitate is solubilised in a solution of a strong mineral acid, then treated with a quaternary ammonium halide and further treated with a water-soluble salt.

These prior art processes have various disadvantages, for example, some require large amounts of energy if the water-miscible solvent is to be separated from the bulk of the aqueous residue after removal of the polysaccharide and the present invention discloses a process which is far less extravagant in the use of energy and can, in a preferred form, involve recycling of the component chemicals involved in the process.

This invention is based on the discovery that by adapting certain multiphase systems, aqueous solutions containing polysaccharides can be caused to throw out the polysaccharide in a form in which it can be readily separated from the aqueous mixture.

In the book "Advances in Liquid Crystals", Vol I, edited by Glenn H. Brown and published by Academic Press in New York in 1975, phase diagrams are considered for various systems including water, fatty acid salts and alcohols.

The zones of compatibility are discussed and referred to in the phase diagrams by the letter L. In some cases the zones are split by other areas having different physical properties and the compatible zones are then indicated by $L_1$ and $L_2$.

DESCRIPTION OF THE INVENTION

It has now been found that within the boundaries of these L zones aqueous solutions containing polysaccharides can be caused to precipitate out the polysaccharide and enhance its separation from the aqueous mixture.

Accordingly, the present invention provides a process for the separation of a polysaccharide from an aqueous solution in which the polysaccharide is separated from the aqueous solution by mixing with the aqueous polysaccharide an amount of a water-soluble fatty acid salt, which fatty acid is substantially insoluble in water and, optionally, a precipitant liquid in which the amounts are sufficient to produce an isotropic mixture in the above defined L zone and to cause separation of the polysaccharide from the mixture.

In a preferred form of the invention, the amounts of both the precipitant liquid and fatty acid salt employed are such as to minimise each addition to the separation mixture. In a further preferred form of the process the precipitant liquid residue is acidified to regenerate the fatty acid and the acidified mixture phase separated to generate a precipitant liquid phase containing the fatty acid and an aqueous phase.

In a further preferred form of the invention the precipitant liquid phase and fatty acid are neutralised and re-used in a further separation process.

The application of this invention is illustrated in the accompanying ternary phase diagrams and, as will be considered in greater detail later, the separation will preferably take place in the area of the diagram with the highest concentration of water and polysaccharide, hence minimising the use of the other components, namely the optional precipitant liquid and the water-soluble fatty acid salt.

The process provided by this invention is particularly useful in the preparation of Biopolymer PS 87 as disclosed in U.S. Pat. No 4,329,448. In addition, the process can be applied to various other polysaccharides and mixtures such as sodium carboxymethylcellulose, various alginates, dextran, xanthan gum and other gums and microbial polysaccharides.

The precipitant liquid should be substantially water-immiscible. Suitable liquids include butanol, pentanol, hexanol, octanoic acid, ethyl acetate, diethyl ether and methyl ethyl ketone.

Many other liquids can also be used as the precipitant liquid and these can be found by a simple test.

Liquids or liquid mixture which are to be considered as precipitant liquid, which are not miscible with water in all proportions, are mixed in varying ratios of liquid, water and fatty acid salt, in order to map out the isotropic liquid phase L or $L_1$ of the ternary diagram. The water component is then replaced with a selected polysaccharide solution in water and the above region tested for phase separation of the polysaccharide in order to define the working zones and the preferred working zones of the invention. The zones preferred relate to immediate precipitation. Outside these zones precipitation either does not occur or occurs more slowly close to the boundaries.

The fatty acid should also be substantially water-insoluble and the preferred fatty acids are those having a $C_8$–$C_{10}$ carbon chain, since their salts do not produce large amounts of foam during the separation process.

The normal concentration of polysaccharide in the systems to be treated by this process, will be in the range 0.01–15% in water, although it will be understood that even trace amounts of polysaccharide can be removed. This range will clearly be related to the solubility of the polysaccharide in water and to the maximum viscosity of such a solution which can usefully be handled in the equipment.

In the accompanying drawings which are ternary diagrams comprising polysaccharides in water, precipitant liquid and water-soluble fatty acid salt, FIG. 1 illustrates a system comprising aqueous dextran T500, butan-1-ol and sodium n-octanoate.

Figure 2:
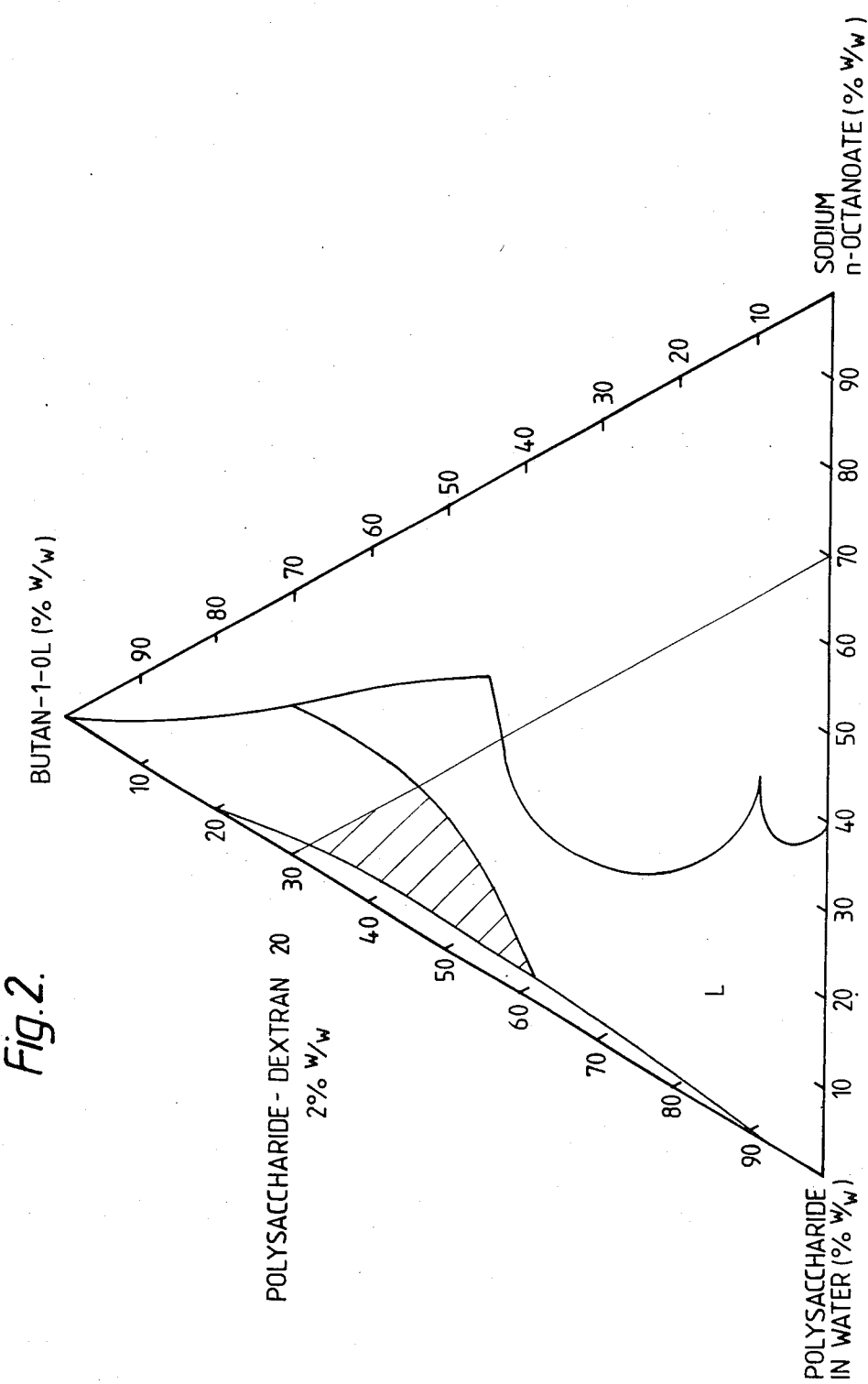

FIG. 2 illustrates a system comprising dextran 20 in water, butan-1-ol and sodium n-octanoate, which precipitate in the same general area.

Figure 3:
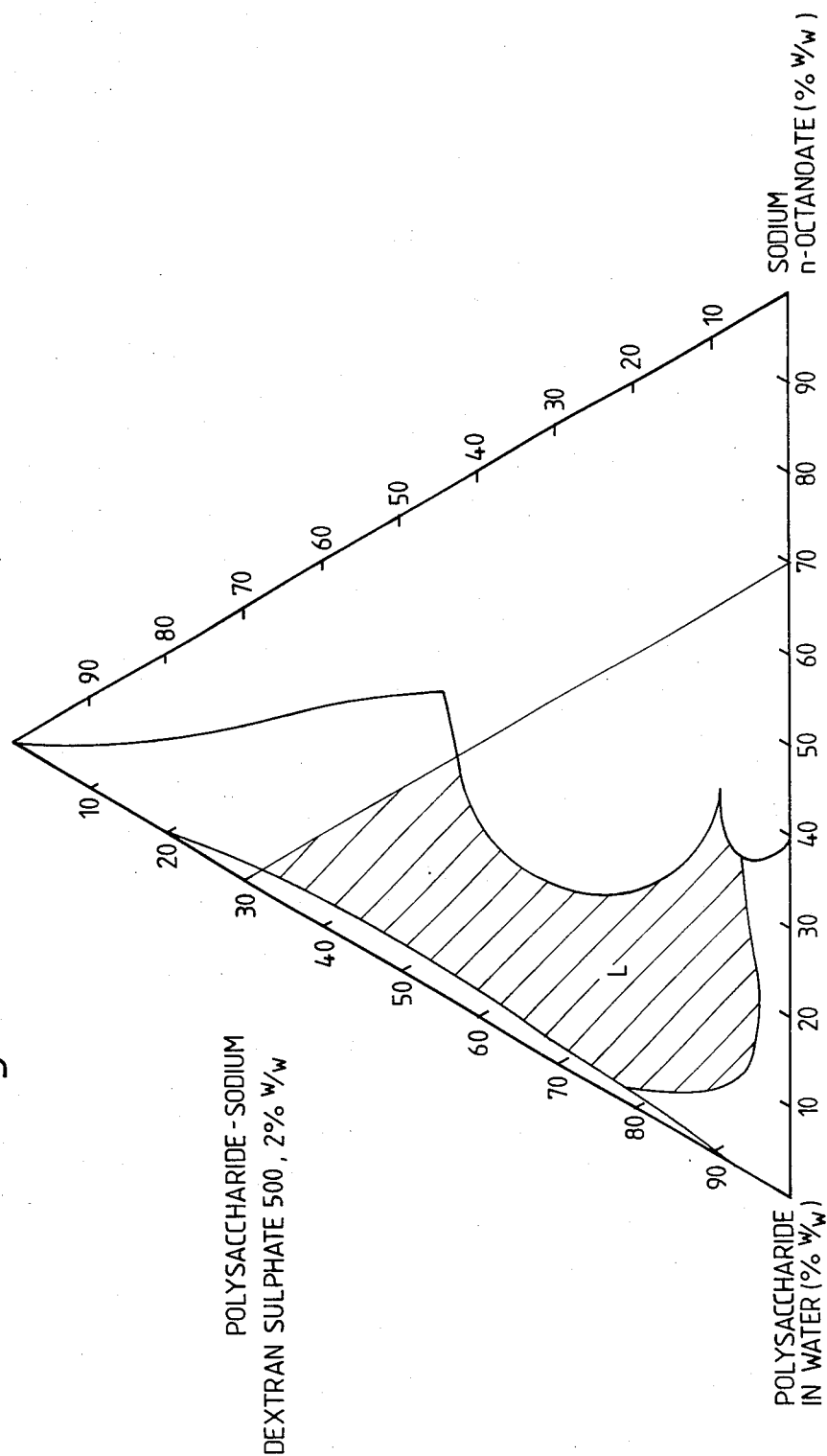
Figure 4:
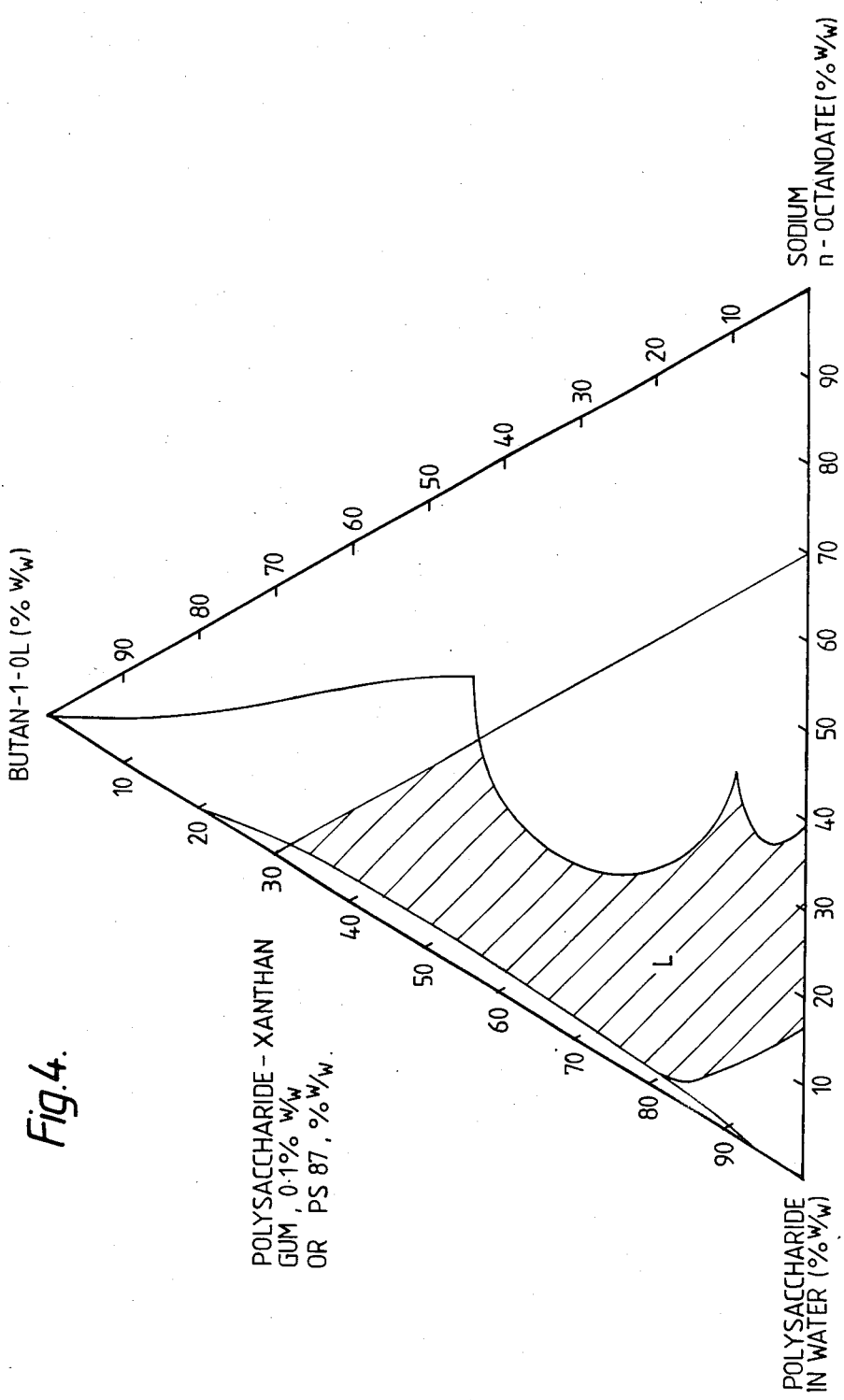

FIG. 3 comprises aqueous dextran sulphate 500, butan-1-ol and sodium n-octanoate and FIG. 4 illustrates a system comprising either xanthan gum or polymer PS87 in water with butan-1-ol and sodium n-octanoate.

Figure 5:
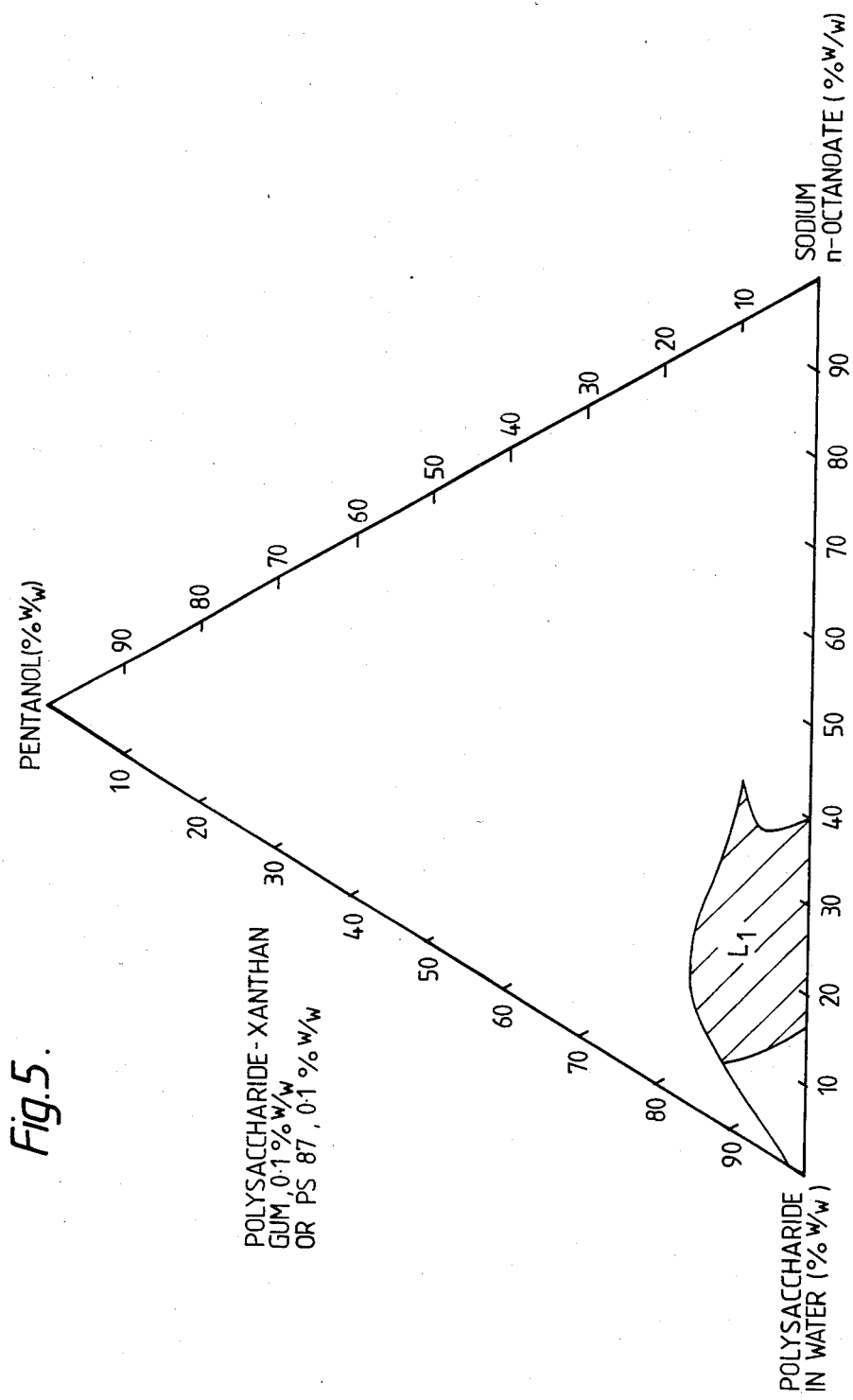

FIG. 5 is similar to FIG. 4 except that pentanol was used instead of butan-1-ol.

Figure 6:
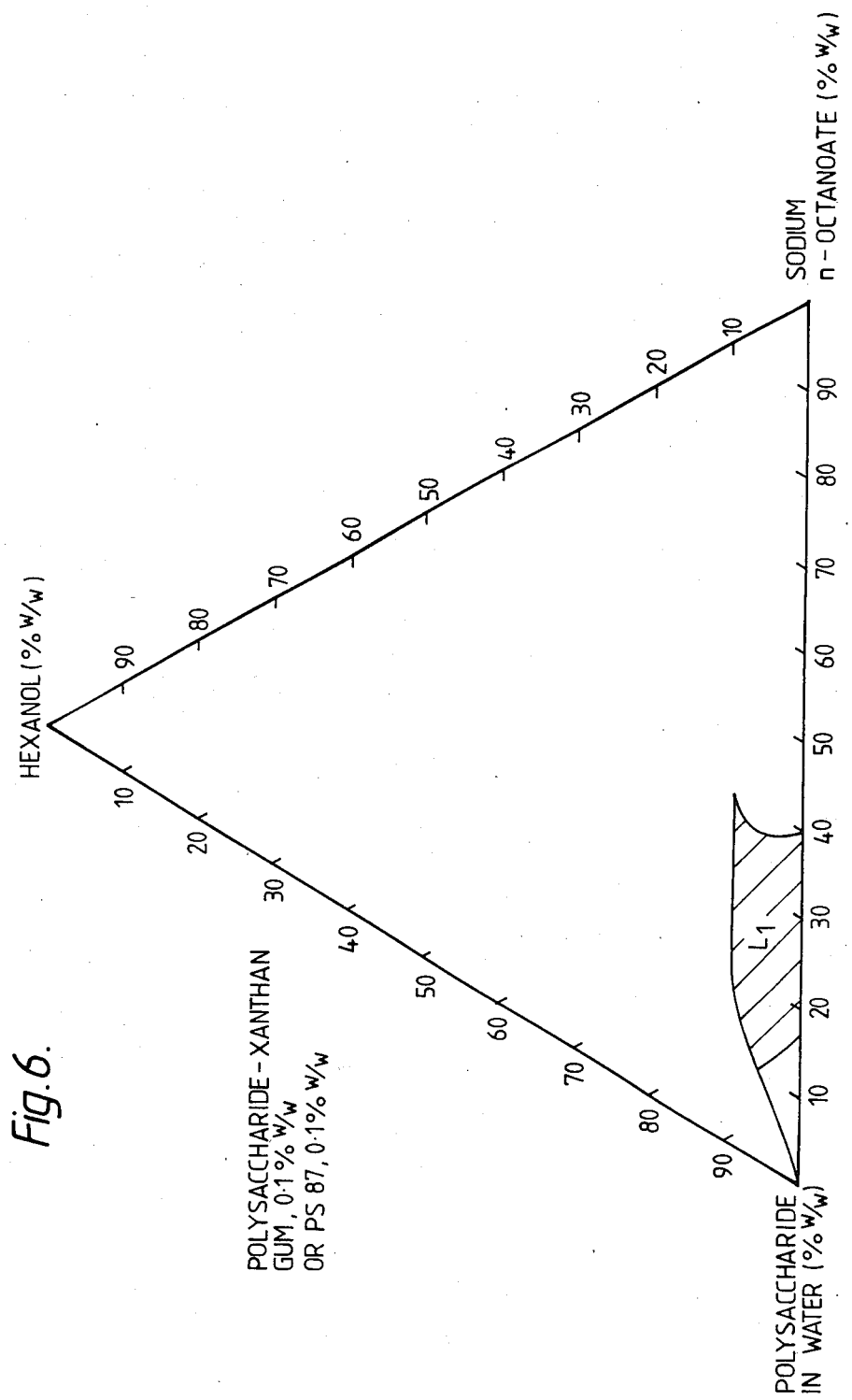

FIG. 6 replaces the pentanol of FIG. 5 with hexanol and

Figure 7:
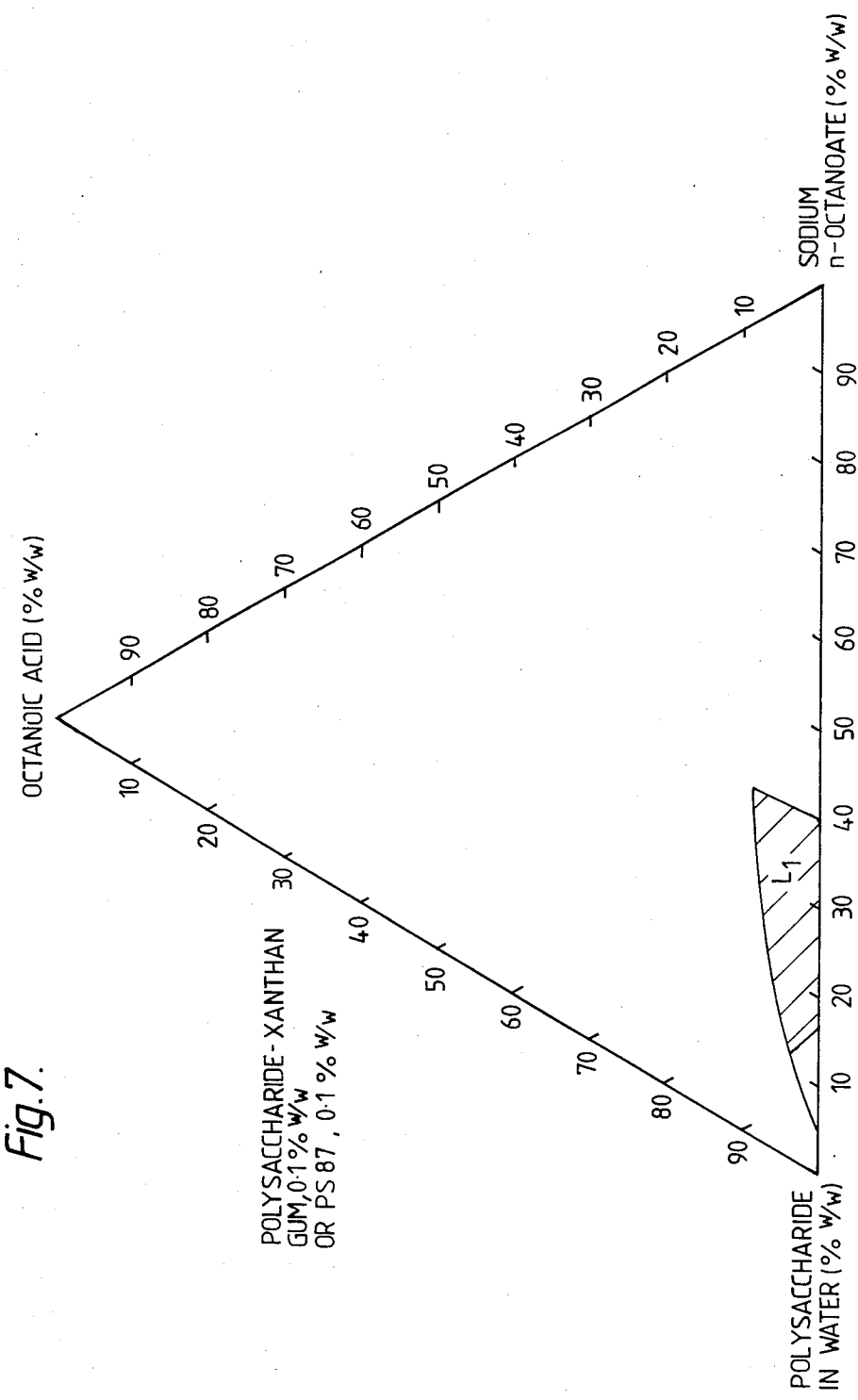

FIG. 7 replaces the hexanol of FIG. 6 with octanoic acid as the precipitant liquid.

The polysaccharides illustrated were dextran T500 ($\overline{M}w$ 500,000), dextran 20 ($\overline{M}w$ 20,000), sodium dextran sulphate 500 ($\overline{M}500,000$), xanthan gum and Biopolymer PS87 as disclosed in U.S. Pat. No 4,329,448. To obtain these phase diagrams compositions were prepared on a 10 cm$^3$ scale. Known weights of polysaccharide solution were taken to which were added, for example, butan-1-ol as the precipitant liquid, and sodium n-octanoate as the water-soluble fatty acid salt, in weighed amounts at water:butanol:octanoate ratios to coincide with the isotropic L or L$_1$ phase of the ternary diagram. The mixtures were rotated for approximately 5 minutes until dissolved and then assessed visually for turbidity indicative of polymer phase separation. The boundary defining the phase separation zone across the L phase in the aqueous polysaccharide/precipitant liquid/ fatty acid salt ternary diagrams are shown in the 7 accompanying figures.

The cross-hatched areas in the drawings in the L or Ll zones ihdicate the areas in which precipitation of the polysaccharides occurs in the various mixtures according to this invention. AAs mentioned earlier, the preferred zones are those in which the addition of fatty acid salts and precipitant liquid are minimised and, hence, are in the lower left-hand corner of the diagrams.

In FIGS. 1 to 4 the line limiting the butanol and sodium n-octanoate content of the mixture indicates the approximate upper limit in which benefits from the invention can be obtained, although it will be understood that some effect may be obtained outside the cross-hatched areas of zones L away from the water-rich areas.

It will be observed that in the mixtures shown in FIGS. 5 to 7 the optional nature of the precipitant liquid is illustrated since the cross-hatched zones include the polysaccharide water/sodium n-octanoate axis.

DETAILED EXAMPLES

Example 1

1.0 g of a 1% w/w aqueous solution of Biopolymer PS87, as disclosed in U.S. Pat. No 4 329 448, prepared by batch fermentation of a sucrose/yeast extract media with Bacillus polymyxa NClB 11429, was mixed with 1.0 g pentan-1-ol. The sample was immiscible and no precipitation of the polysaccharide was observed. 8.0 g of 30% w/w sodium n-octanoate in water were added which resulted in a clear homogeneous liquid phase with formation of a dense fibrous precipitate of the polysaccharide.

Example 2

10 g mixtures of 1% w/w Biopolymer PS87, water, pentan-1-ol and 30% w/w sodium n-octanoate were taken such that the final concentration of PS87 in the mixture was 0.1% w/w and the ratio of water:octanoate:alcohol varied across the water.rich isotropic region of the phase diagram. The samples were mixed by end over end rotation, left to stand overnight and assessed visually for formation of a fibrous precipitate of polysaccharide. The results are given in Table 1.

TABLE 1

| % Octanoate | % Pentanol | Precipitation |
| --- | --- | --- |
| 0 | 0 | No |
| 5 | 3 | No |
| 6 | 4 | No |
| 6 | 5 | No |
| 7 | 2 | No |
| 7 | 4 | No |
| 8 | 7 | Partial |
| 8.5 | 1 | No |
| 9 | 10 | Yes |
| 10 | 2 | No |
| 10 | 3 | No |
| 11 | 8 | Yes |
| 12 | 5 | Yes |
| 13 | 6 | Yes |
| 14 | 0 | Partial |
| 15 | 2 | Yes |
| 15 | 3 | Yes |
| 17 | 1 | Yes |
| 24 | 1 | Yes |

EXAMPLE 3

Equal weights 25 g of xanthan gum solution (1.5% w/w)( and 1:1:3 pentan-1-ol:sodium n-octaneoate:water were thoroughly mixed. The resulting precipitate was filtered. The filtrate was treated with sulphuric acid to pH 2.2 and centrifuged (3000 rpm for 15 minutes). The recovered organic phase was removed, treated with caustic soda (1.3 g) diluted to 25 g with distilled water and adjusted to pH 7.5 by addition of sulphuric acid.

This solution was added to a second aliquot (25 g) of xanthan gum solution (1.5% w/w) and the above procedure was repeated. Precipitation of a third aliquot required a reconcentrating of the organic due to losses on recovery.

Example 4

6.0 g of 2% w/w solution of dextran sulphate ($\overline{M}w$ 500,000) in water were mixed with 3.1 g sodium n-octanoate and 0.2 g butan-1-ol. The sample was mixed by end over end rotation to produce a clear homogeneous solution. No phase separation occurred.

Addition of a further 0.5 g butan-1-ol led to the formation of a turbid mixture from which separated a clear viscous polymer phase on standing.

Example 5

4.0 g of 10% w/w dextran ($\overline{M}w$ 500,000) in water were mixed with 2.0 g sodium n-octanoate and 4.0 g butan-1-ol. The sample was mixed by end over end rotation to produce a clear homogeneous solution. No phase separation occurred.

Addition of a further 1.4 g butan-1-ol led to the formation of a turbid mixture from which separated a clear viscous polymer phase on standing.

Example 6

4.9 g of 1% w/w xanthan gum in water were mixed with 4.0 g of 30% w/w sodium n-octanoate in water and 1.0 g ethyl acetate. Precipitation of a dense fibrous polymer phase occurred immediately leaving a clear liquid phase.

Example 7

7.9 g of 0.5% w/w xanthan gum in water were mixed with 1.3 g of sodium n-octanoate and 1.1 g of diethyl ether. Precipitation of a dense fibrous polymer phase occured immediately leaving a clear liquid phase.

Example 8

6.9 g of 9.5% w/w xanthan gum in water were mixed with 0.7 g of sodium n-octanoate and 2.5 g of butanone (methyl ethyl ketone). Precipitation of a dense fibrous polymer phase occurred immediately leaving a clear liquid phase.

We claim:

1. A process for the separation of a polysaccharide from an aqueous solution in which the polysaccharide is separated from the aqueous solution by mixing with the aqueous polysaccharide an amount of water-soluble fatty acid salt, which fatty acid is substantially insoluble in water, in an amount sufficient to produce an isotropic mixture in a defined L phase zone and to cause phase separation of the polysaccharide from the mixture leaving the fatty acid salt in solution.

2. A process as claimed in claim 1 in which a precipitant liquid is also used and effective amounts of both the precipitant liquid and fatty acid salt are employed in such amounts to minimize addition of each to the separation mixture.

3. A process as claimed in claim 2 in which process the liquid remaining after separation of the polysaccharide is acidified to regenerate the fatty acid.

4. A process as claimed in claim 3 in which the resulting acidified mixture is separated to generate a precipitant liquid phase containing the fatty acid and an aqueous phase.

5. A process as claimed in claim 1 which the fatty acid is a $C_8$ to $C_{10}$ carbon chain length fatty acid.

6. A process as claimed in claim 1 in which the polysaccharide is selected from the group consisting of Biopolymer PS87, sodium carboxymethyl cellulose, alginates, dextran, xanthan gum and microbial polysaccharides.

7. A process as claimed in claim 2 in which the precipitant liquid is selected from the group consisting of butan-1-ol, pentanol, hexanol and octanoic acid.

* * * * *

UNITED STATES PATENT AND TRADEMARK OFFICE
CERTIFICATE OF CORRECTION

PATENT NO. : 4,810,787
DATED : March 7, 1989
INVENTOR(S) : Garvey et al

It is certified that error appears in the above-identified patent and that said Letters Patent is hereby corrected as shown below:

On The Title Page, Item [73] should read
-- Assignee: Unilever Patent Holdings BV --.

Signed and Sealed this

Twenty-sixth Day of September, 1989

Attest:

DONALD J. QUIGG

Attesting Officer

Commissioner of Patents and Trademarks